United States Patent
Ritman

(10) Patent No.: US 7,688,944 B2
(45) Date of Patent: Mar. 30, 2010

(54) SYSTEM AND METHOD FOR TIME-OF-FLIGHT IMAGING

(75) Inventor: Erik Leo Ritman, Wabasha, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 141 days.

(21) Appl. No.: 11/994,040

(22) PCT Filed: Jul. 3, 2006

(86) PCT No.: PCT/US2006/026090

§ 371 (c)(1),
(2), (4) Date: Jun. 3, 2008

(87) PCT Pub. No.: WO2007/005901

PCT Pub. Date: Jan. 11, 2007

(65) Prior Publication Data

US 2009/0116720 A1    May 7, 2009

Related U.S. Application Data

(60) Provisional application No. 60/696,385, filed on Jul. 1, 2005.

(51) Int. Cl.
*G01N 23/04* (2006.01)
*H05G 1/64* (2006.01)
(52) U.S. Cl. ........................ 378/62; 378/98.8
(58) Field of Classification Search ............ 378/4, 378/19, 62, 98.8; 250/370.09; 382/132
See application file for complete search history.

(56) References Cited

U.S. PATENT DOCUMENTS

| | | | |
|---|---|---|---|
| 4,075,482 | A | 2/1978 | Perilhou |
| 5,532,489 | A | 7/1996 | Yamashita et al. |
| 5,576,545 | A | 11/1996 | Stoub et al. |
| 5,583,908 | A | 12/1996 | Antich et al. |
| 5,610,396 | A | 3/1997 | Mattern |
| 6,180,946 | B1 | 1/2001 | Ebstein |
| 6,423,971 | B1 | 7/2002 | Yamakawa |
| 6,858,847 | B1 | 2/2005 | Macciocchi |

(Continued)

OTHER PUBLICATIONS

International Search Report and Written Opinion under date of Feb. 2, 2007 in connection with International Patent Application No. PCT/US2006/26090.

*Primary Examiner*—Irakli Kiknadze
(74) *Attorney, Agent, or Firm*—Quarles & Brady LLP

(57) ABSTRACT

A system and method for imaging a subject includes a clock that generates a clock signal and a radiation source that directs photons through the subject in response to the clock signal. A detector system is included that detects the photons and a memory module records a time of detection of the photons by the detector system with respect to the clock signal. The system includes a processor that calculates a time of flight (TOF) of the photons from the radiation source to the detector system and compares the TOF to a reference TOF to determine a delay in the TOF attributable to the photons passing trough the subject.

20 Claims, 8 Drawing Sheets

U.S. PATENT DOCUMENTS

| | | |
|---|---|---|
| 7,252,789 B2 * | 8/2007 | Venkataramani et al. ............... 252/301.4 R |
| 2001/0017352 A1 | 8/2001 | Stark |
| 2002/0057760 A1 | 5/2002 | Carroll et al. |
| 2003/0006376 A1 * | 1/2003 | Tumer ................. 250/370.09 |
| 2003/0210760 A1 * | 11/2003 | Nelson ........................ 378/4 |
| 2004/0036025 A1 | 2/2004 | Wong et al. |
| 2004/0065838 A1 * | 4/2004 | Tumer ................. 250/370.09 |
| 2005/0104001 A1 | 5/2005 | Shah |

* cited by examiner

SYSTEM AND METHOD FOR TIME-OF-FLIGHT IMAGING

CROSS REFERENCE TO RELATED APPLICATIONS

This application represents the national stage application of International Application PCT/US2006/026090, filed 3 Jul. 2006, which is based on U.S. Provisional Patent Application Ser. No. 60/696,385 filed on Jul. 1, 2005, and entitled "EXPLORATION OF TIME OF FLIGHT X-RAY IMAGING (TOFXI)".

STATEMENT REGARDING FEDERALLY SPONSORED RESEARCH

N/A

BACKGROUND OF THE INVENTION

The present invention relates generally to a system and method for generating high-quality x-ray images using relatively small radiation doses. In particular, the present invention includes a system and method for generating x-ray images by utilizing time-of-flight information to derive contrast information. This time-of-flight information is derived by measuring the refractive index (i.e., ratio of x-ray velocity through matter as compared to velocity through a vacuum) of x-rays through a body, which can then be used to reconstruct an image of the body.

X-ray imaging is a common and powerful technique for non-invasive evaluation of a patient. Traditional x-ray images are generated by correlating the amount of attenuation experienced by x-rays passing through a subject to the type of material through which the x-ray passed. In particular, x-rays are stopped in tissues by way of energy transfers from the x-ray photons that occur roughly in proportion to the amount of material through which the x-ray passes. Consequently, the amount of attenuation experienced by an x-ray beam passing through a body forms a "signal" that is then used to generate an x-ray image. Hence, the "signal" used to generate an x-ray image is actually the lack or absence of energy or photons detected when an x-ray beam is passed through a patient.

The use of the lack of photons detected as the "signal" from which an image is generated presents a number of inherent problems. In particular, the number of photons illuminating a body varies randomly about a mean value. In this regard, more information can often be acquired using a higher dose of radiation (i.e. stronger x-ray beam) because a greater dynamic range of information is available. That is, it is desirable to have a very high number of photons (e.g., a million) "illuminating" a selected location in the body (e.g., 1 mm$^2$) corresponding to each pixel in an image to ensure that there is a certain fractional reduction in the number of photons. Simply, image spatial and contrast resolution increase depends on the number of detected x-ray photons per image pixel.

However, high doses of radiation are typically undesirable due to the x-ray's potential to damage the body. In particular, there is a direct relationship between the number of x-ray photons interacting with tissue and the increased risk of radiation-induced tissue damage and cancer development. In traditional x-ray imaging systems that rely upon attenuation-based x-ray imaging, a dilemma is created between the need for increased contrast achieved using elevated radiation doses and the potential for damage that such doses can yield.

In an effort to overcome this problem, contrast agents are often introduced to better delineate certain anatomic features. However, these contrast agents also carry some risks.

Furthermore, enhancement of traditional x-ray imaging is limited to incremental reduction of radiation exposure. As a result, various systems and methods have been employed for increasing contrast resolution while minimizing x-ray dose. For example, one method modulates x-ray tube current (mA) as a function of beam angle with respect to the patient. Other systems have employed monochromatic radiation, rather than bremstrahlung radiation. Furthermore, some systems have attempted K-edge subtraction imaging and/or used photon counting (as opposed to traditional energy integrating) detector systems.

Unfortunately, these attempts for reducing radiation exposure in traditional x-ray imaging systems have been only somewhat successful. For example, modulating x-ray tube current as a function of beam angle relative to the patient, while first proposed in the mid 1980s, still has not been found to be compelling. Similarly, while monochromatic x-ray systems can reduce the effective dose at the chest by 18.7% and the dose to the head by 1.2%, at the same time, the dose delivered to the lumbar spine is increased by 38.3%, as is the dose delivered to intra-abdominal organs by 35-47%. Also, systems employing K-edge subtraction imaging and/or photon counting detectors have also been shown to decrease x-ray exposure needed to achieve a certain x-ray image quality. A major problem here is that tuneable monochromatic x-ray sources are still not routinely available for clinical use.

Recent developments, for example, in synchrotron x-ray-based imaging, have indicated that utilizing the differences in refractive index of x-rays (i.e., indicators of variations in the velocity of x-ray as they travel through different substances), rather than attenuation, as the imaging "signal" may greatly decrease the x-ray dose needed to reconstruct clinically useful images. As illustrated in FIG. 1, the refractive index of x-rays ($\rho$) with 12-24 kilo-electron volts (keV) 10, 12 serve as a much stronger "signal" than attenuation ($\mu$) with 12 keV x-rays 14 or 24 keV x-rays 16. This is particularly true for elements having a low atomic number, which are more biologically relevant to clinical analysis.

While clearly being theoretically advantageous, velocity-based imaging systems have not been widely realized due to various formidable hurdles to actual implementation. In particular, while previously demonstrated as operable by imaging small specimens, systems have not been successfully developed that are appropriate for humans or full body imaging.

For example, one approach to make a system suitable for imaging humans is to "scale up" the refraction and phase contrast imaging methods developed for small-specimen imaging in an attempt to make them suitable for whole body imaging. These approaches are faced, however, with the problem of "unraveling" the many changes in refraction (expressed as phase shifts) that occur as the photon passes through 30 cm or more of tissue. For example, at 17.5 keV, 50 micrometers ($\mu$m) of water causes a 180 degree phase shift. Hence, for a 30 centimeter (cm) human abdomen, 6000 phase shifts would be expected, which is computationally cumbersome, if not currently impossible, to "unravel".

A similar approach uses a Bonse Hart interferometer, which has been shown to successfully perform phase imaging of small specimens at relatively low keV. However, to implement this approach, a perfect silicon crystal is needed, which is difficult and costly to produce at the large scales necessary to image humans. Additionally, this method involves the use of Bragg diffraction to acquire a reference beam against which the beam transmitted through the object is compared. In this case, the optic path length of the reference beam should be stable to within 0.1 nanometer (nm), which presents another significant technological impediment to implementation. Therefore, phase-delay imaging, which utilizes the interference patterns resulting from coherent x-rays passing through different tissues, is suitable only for very small diameter specimens (e.g., 1 mm) and requires synchrotron radiation.

Other approaches involve the use of an x-ray Talbot interferometer or of an "analyzer" crystal that allows measurement of the angle of refraction of x-rays, which is used to generate an image with edge enhancement effects. In the former case, an object is imaged using coherent illumination passing through a phase grating. To perform the latter, a method commonly referred to as "Diffraction Enhanced Imaging" (DEI) is used to generate a transmission image with edge enhancement effect caused by the slight refraction of the x-rays in regions with rapid change of refractive index, such as occurs at the surface of collagen fibers and blood vessels.

However, each of these methods, as well as the others described above, rely on rather low energy x-ray photons (approximately 10-30 keV) having relatively long wave lengths because the low energy x-ray photons yield more obvious interference patterns and greater refraction deviation. The lower energy x-ray photons are not suitable for imaging larger human subjects because the majority of the photons are stopped by the long tissue path lengths. Thus, while these methods have been demonstrated as feasible on small specimens, they are not clinically viable for human patients.

Therefore, it would be desirable to provide a system and method for significantly reducing x-ray exposure while still producing an image of sufficient quality to be clinically useful. Moreover, it would be desirable to have a system and method for measuring variations in the transit times of x-ray photons as they traverse a relatively large body, such as a human body.

SUMMARY OF THE INVENTION

The present invention overcomes the aforementioned drawbacks by providing a system and method for producing an x-ray image using a significantly reduced radiation dose. The present invention facilitates time-of-flight imaging (TOFI) of relatively large bodies (e.g., a human body) to provide a set of information from which to reconstruct an image of the body. In particular, the present invention measures the refractive index (i.e., ratio of x-ray velocity through matter as compared to velocity through a vacuum) of x-rays through the body and utilizes this information to reconstruct an image of the body. As such, the present invention is capable of reducing x-ray exposure by orders of magnitude, because the contrast conveyed by the refractive index of x-rays through soft tissues is considerably greater than that obtained with traditional x-ray imaging.

According to one embodiment of the present invention, an imaging system includes a clock that generates a clock signal and a radiation source that directs photons through a subject to be imaged in response to the clock signal. A detector system is included that detects the photons and a memory module records a time of detection of the photons by the detector system with respect to the clock signal. The system includes a processor that calculates a time of flight (TOF) of the photons to the detector system and compares the TOF to a reference TOF to determine a delay in the TOF attributable to the photons passing trough the subject.

Various other features and advantages of the present invention will be made apparent from the following detailed description and the drawings.

BRIEF DESCRIPTION OF THE DRAWINGS

FIG. 4b is a graph showing a predicted frequency histogram over time of the probability graph of FIG. 4a;

DETAILED DESCRIPTION OF THE PREFERRED EMBODIMENT

It is contemplated that a variety of techniques may be employed to perform time-of-flight imaging (TOFI) to image large scale subjects, such as human patients. In particular, three systems usable with two detector systems will be described for clinically applicable imaging of the x-ray refractive index of tissues.

Figure 1:
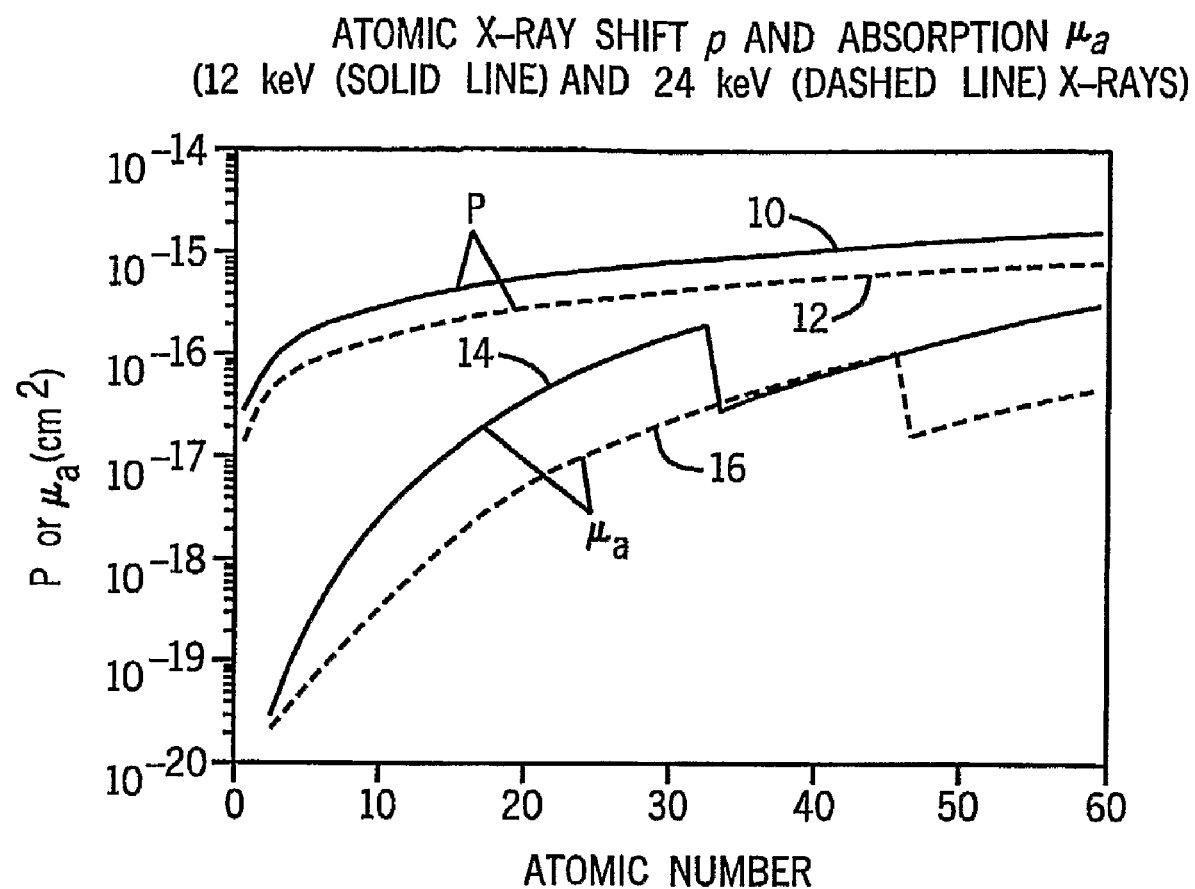
FIG. 1 is a graph showing refraction and attenuation of x-rays as a function of atomic number.
Figure 2:
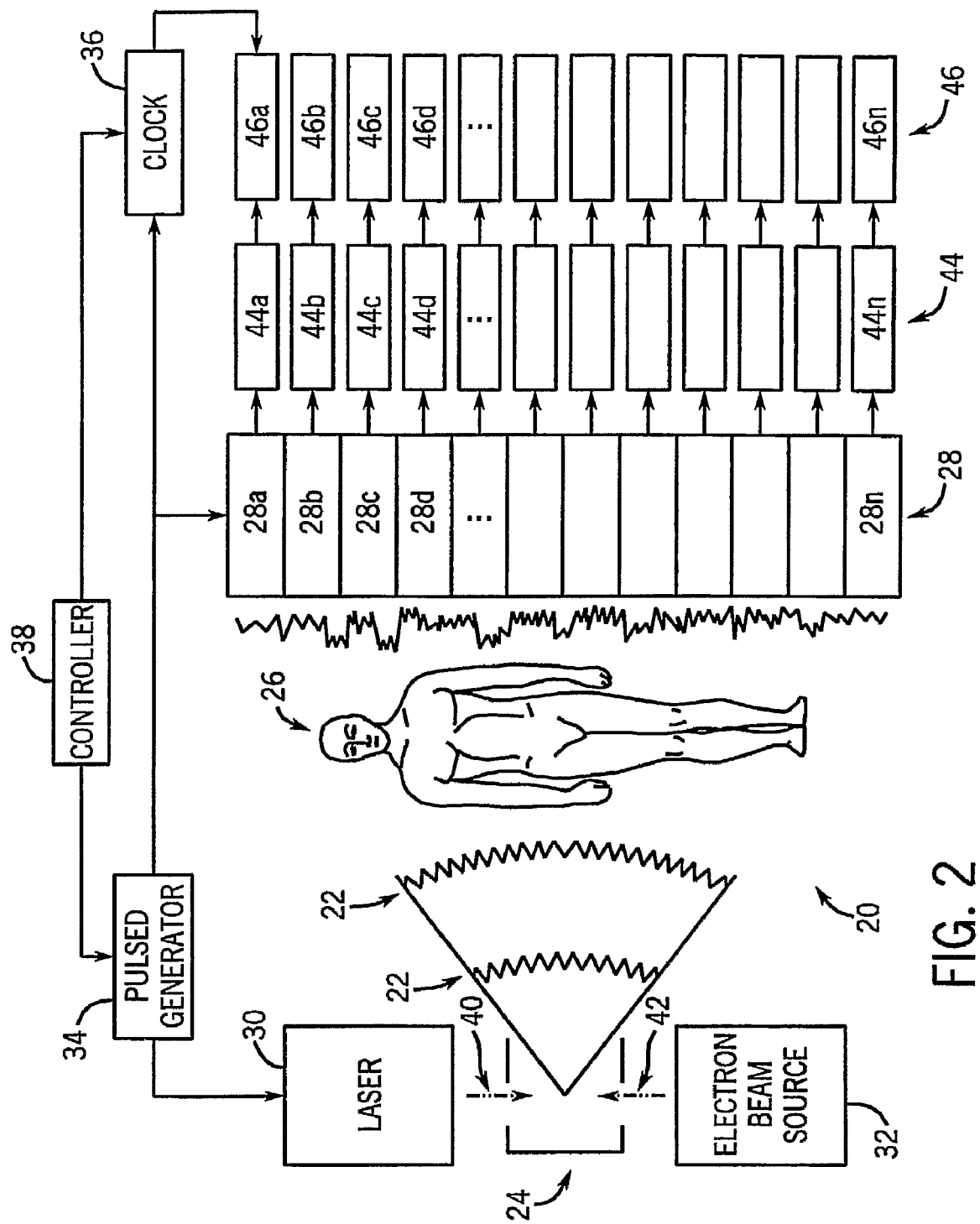
FIG. 2 is a schematic representation of one system for performing time-of-flight x-ray imaging.

Referring to FIG. 2, in accordance with one aspect of the invention, one system 20 for performing TOFI is designed to generate a brief x-ray pulse 22 and measure the time of flight from a source 24, through a subject 26, and to a detector system 28. The high intensity x-ray pulse 22 can be generated by aiming a high power laser 30 directly at an oncoming electron beam source 32 to form the source 24. A pulse generator 34 is controlled in conjunction with a clock 36 by a controller 38 to cause the laser 30 to emit periodic pulses of laser light 40. The laser light 40 emitted by the laser 30 collides with and slows down the electrons of an electron beam 42 emitted by the electron beam source 32, which results in the generation of the x-ray pulse 22. Hence, the x-ray pulse 22 will have a temporal intensity distribution that can be controlled based on the laser pulse 40 generated by the laser 30. Additionally or alternatively, it is contemplated that a free electron laser (not shown) may be used to generate the x-ray pulse 22.

Figure 3:
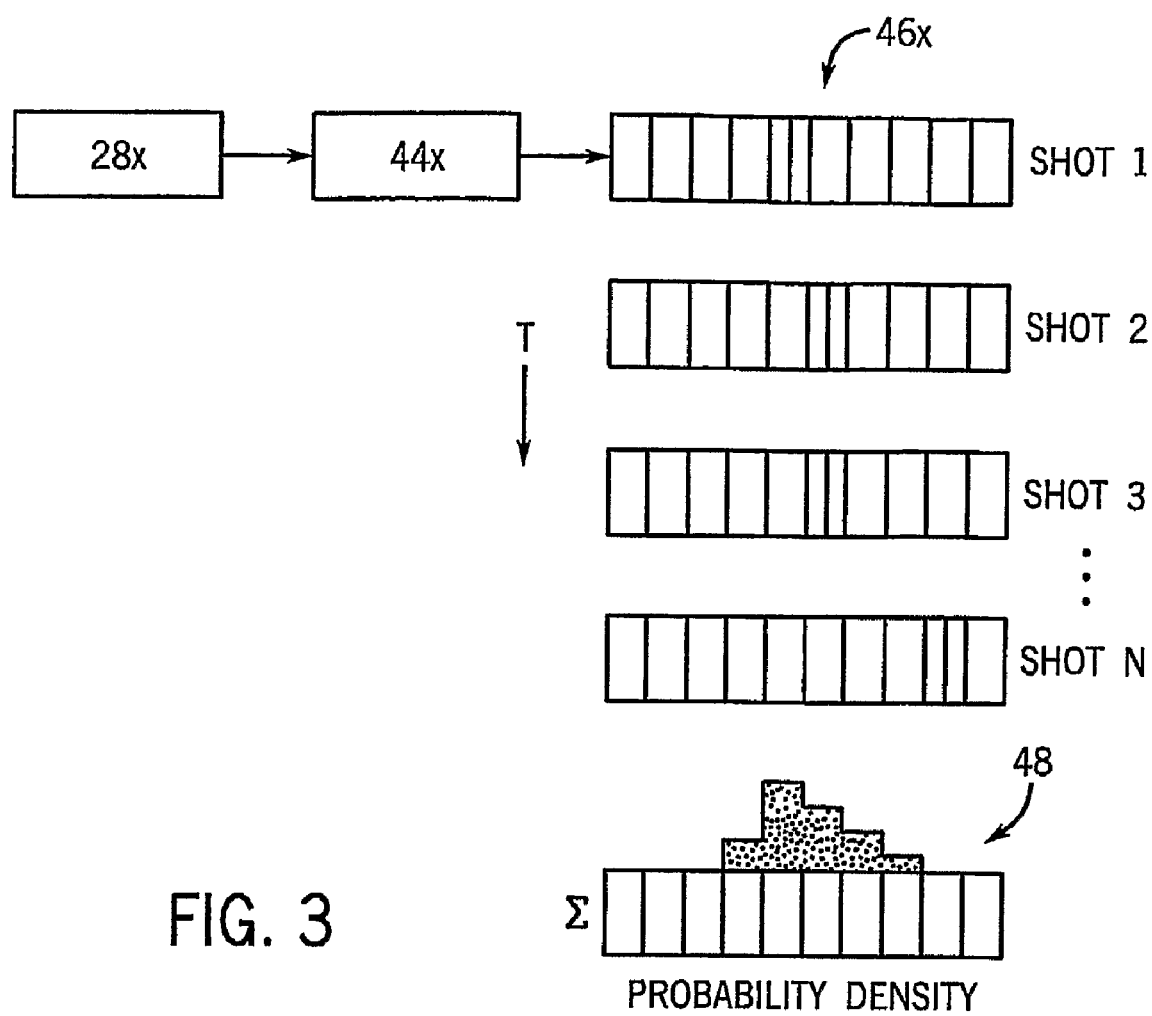
FIG. 3 is a schematic representation of a single component of the detector array for repeated use in the system of FIG. 2.

The x-ray pulse 22 is convolved with the spread in detection times inherent in the detection of x-ray photons 22 at the detector system 28. In particular, the system must accommodate the inherent time-spread in the x-ray launch time, the time-spread in the detection of an arrival event of an x-ray photon at the detector, and the limited time-resolution of event-detector clocks. Referring to FIGS. 2 and 3, the variability of photon detection time across each different detector 28a through 28n is tracked using a trigger 44, for example a Schmidt trigger, associated with each detector 28a-28n. As will be described, the triggers 44 indicate the instance when a photon is detected at a given detector 28a-28n, which is then stored as a recorded time of detection by an associated register 46. In particular, the register 46 associated with each element in the detector 28 acts as an accumulator that counts the pulses received from the clock 36 until the trigger 44 is triggered by the detection of a photon at the associated detector element. When the photon is detected, the trigger 44 "freezes" the register 46 and the total number of pulses counted by the register 46 is used to calculate the time delay incurred by the photon due to passing through the subject by comparing the total to a reference value acquired without the subject's presence in the beam field.

As illustrated in FIG. 3, the variability of segmental detections in a single detector 28x can be identified by the associated trigger 44x and tracked by monitoring the values held by the register 46x over time. A number of contiguous time slots can be added to generate a frequency histogram 48 that is used to estimate the true time of arrival of each photon at the face of the detector 28x, as opposed to the variable depth each photon reaches within the detector 28x before being detected.

Figure 4A:
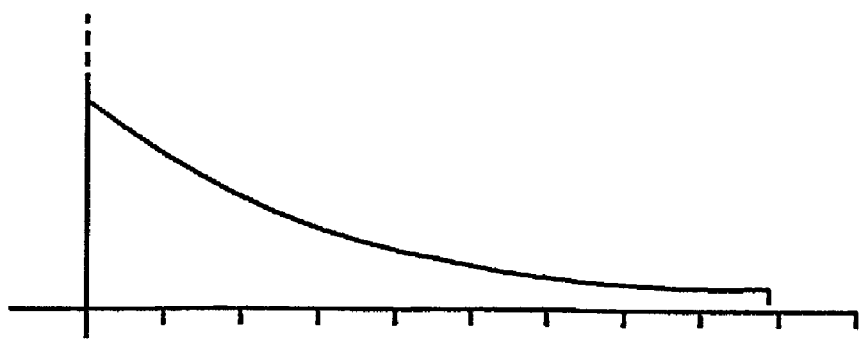
FIG. 4a is a graph showing the probability of an x-ray photon being stopped and detected by a scintillator as a function of photon penetration through the scintillator.
Figure 4B:
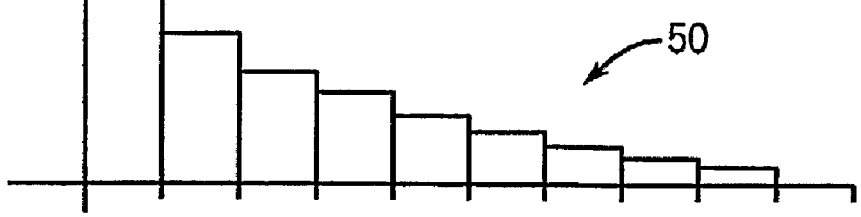
Figure 4C:
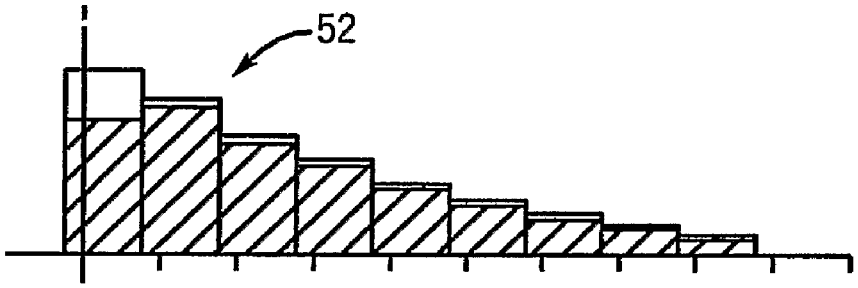
FIG. 4c is a graph showing a potential mismatch from the predicted frequency histogram of FIG. 4b attributable to clock cycle phase mismatch.
Figure 4D:
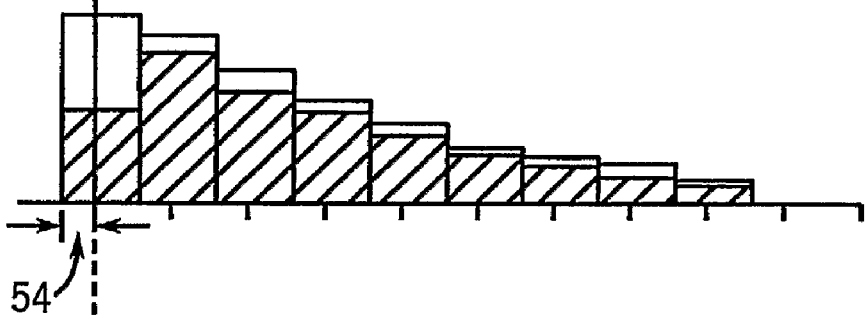
FIG. 4d is a graph showing that the potential mismatch of FIG. 4c can be used to estimate the cycle's phase mismatch by relating the distribution of detected photon events to the known time-distribution that is being detected.

In particular, referring to FIG. 4a, the probability of an x-ray photon being stopped and detected by a given scintillator decreases as it penetrates deeper into the crystal. As shown in FIG. 4b, since this exponential "decay" is predictable and reproducible, the A/D conversion of a particular A/D converter operating at a given frequency results in a predictable frequency histogram 50 of the cumulative signal over time for continuous exposure to x-rays. However, referring to FIG. 4c, when the "clock" cycle is out of phase, by δt, a change in the temporal detection photon occurs, as illustrated by a "mismatched" area 52. Thus, when the A/D distribution of single photon hits are examined, the difference of the pattern over time can be directly related to the sub-resolution time difference. Therefore, as illustrated in FIG. 4d, a number of detections are needed to correctly identify the proportion of phase shift 54 (i.e. δt) and, thus, the altered time distribution as a function of mismatch of the actual probability profiles from the idealized probability profiles. This spread of photon detection times, if stable and well characterized, permits a super-resolution time-of-arrival measurement.

Also, in order to identify photon detections at each element in the imaging array (i.e., unless there is a negligible chance that any one detector has not been exposed by the required minimum number of photons), it is desirable to ensure that some of the detectors will be receiving more photons than necessary. To do so, the number of detector elements that receive less than a predetermined minimum number of hits must be estimated so that a maximum dose is selected that will ensure that each detector has been exposed to the minimum number of photons. However, by utilizing the above-described system, this maximum dose will still be significantly below the minimum dose required in traditional attenuation-based x-ray imaging processes.

For example, if it is desired to detect a time difference of 10 attoseconds, the subject must be exposed to 128×1000/5 (i.e., a radiation exposure that is approximately 20% of that needed to perform a typical attenuation-based method) in at least one element of the detector array. Consequently, in this example, the total exposure required to yield a given resolution would be almost $1/15^{th}$ of the exposure necessary using traditional x-ray attenuation-based imaging methods.

Referring again to FIG. 2, to accurately identify the delay attributable to the x-rays 22 passing through the subject 26, a reference time-of-flight measurement must be acquired. To do so, an "image" is generated with the subject 26 removed from the path of the x-ray beam 22. This "image" is then used to establish a reference timing image for fixed time delays associated with each detector in the detector system 28.

Therefore, in operation, the system 20 generates a very short burst or pulse of x-rays 22 using, for instance, the opposing electron beam 42 and laser 40 arrangements shown in FIG. 2, or a field-emission x-ray source. The arrival times of the pulse 22 at each detector 28a-28n in the detector system 28 is identified by the trigger 44 and stored by a register 46. The time-distribution of the photons within each x-ray pulse should be accurately identified and several pulses may be needed to compensate for the time variability in the pulse's photon-timing distribution, since uncertainty in photon launch-time detracts from the detection timing capability. However, at the same time, the lower photon energy enhances the detection timing capability. Thus, in order to provide statistical data necessary to reconstruct a clinically useful image, the x-ray pulses 22 are iteratively repeated and tracked.

Figure 5:
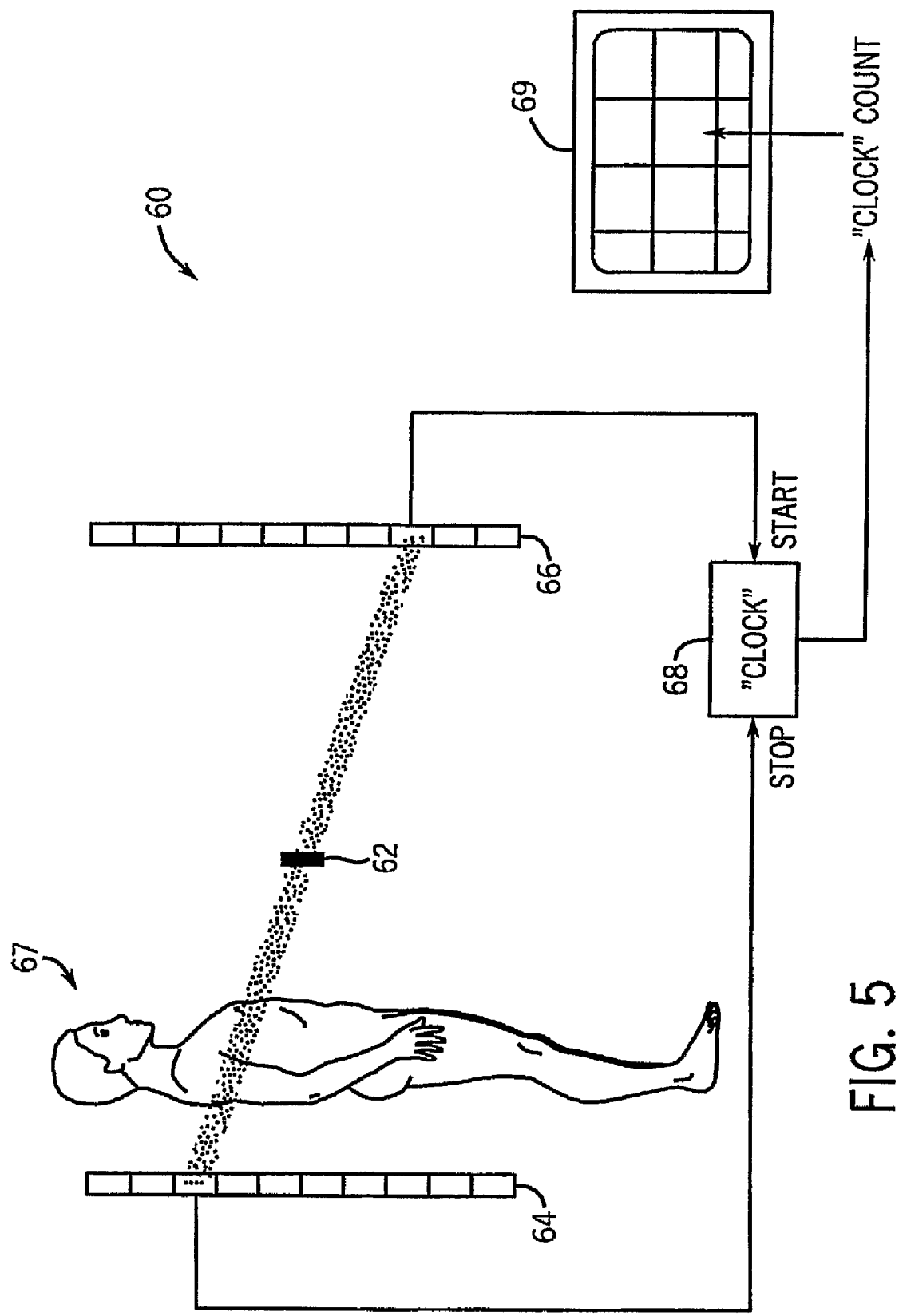
FIG. 5 is a schematic representation of another system for performing time-of-flight x-ray imaging.

Referring now to FIG. 5, another system 60 for performing TOFI includes small volume (for example, less than 1 $mm^3$) positron emitter 62 that may be used to track gamma ray time-of-flight information. The positron emitter 62 is located between two parallel detector arrays 64, 66. A subject 67 is positioned between the positron emitter 62 and one of the arrays 64. This provides the ability to have a null-reading reference image acquired by the other detector array 66, against which the gamma ray photon arrival-delay caused by passing through the subject 67 on the way to the detector 64 can be measured without the need for an absolute time measurement of the "launch" of the photon.

In particular, a clock 68 is used to time the difference between receiving a reference signal at the reference detector 66 and a subject signal at the subject detector 64. Accordingly, the clock 68 generates a "clock count" corresponding to the time difference between receiving the reference signal and the subject signal, which is then used to reconstruct a TOF image of the subject 67.

Any consistent mismatch between the imaging and reference detectors 64, 66 is detectable for those photons that strike the detector without passing through the body (i.e., they have identical values to those in the corresponding reference detector). Accordingly, the need to compensate for the uncertainty in the timing of launching individual photons described above is alleviated.

In accordance with one embodiment, it is contemplated that a radioactive positron emission source may be utilized. However, it is preferable to utilize a 1,022 keV electron source to generate the opposing 511 keV photons via pair-production in a non-radioactive material. In this regard, the amount of radioactivity needed can be estimated. For example, if a 0.1 mm thick detector is used, assuming a detection time uncertainty of less than 330 femtoseconds (which, can be achieved as will be described below) and an attenuation coefficient of 1/cm, only 3% of the incident photons will be detected. The probability when extended across both detectors 64, 66 then drops to a 0.09% chance that a coincidence will be detected by both detectors 64, 66. Accordingly, an exposure of at least 1000 photons per detector element is desirable, which requires 20 by 1000 photon exposure/$mm^2$. It should be noted that this exposure is still only 10% of the exposure required to perform attenuation-based x-ray imaging.

Additionally, within the above-described system 60, the resulting gamma rays, which have a photon energy of 511 keV, only fail to penetrate an adult human torso about 50% of the time. On the other hand, typical clinically used x-rays, having an energy of approximately 50-70 keV, often pass through the average torso at a rate of less than 10%.

However, the use of 511 keV gamma rays requires a level of accuracy in detecting that is extremely taxing and can generate images that are not clinically acceptable. In particular, the refractive index of a material is calculated by the square root of 1 minus X, where X is the susceptibility of the material calculated by $e^2\rho/(\pi m v^2)$, e is the electron charge, $\rho$ is the electron density of the material, m is electron rest mass, and v is the frequency of the gamma ray. To simplify the calculations, the refractive index can be approximated as 1 minus X/2.

Accordingly, if the material being imaged is water, at 10 keV, the refractive index is $1.04 \times 10^{-4}$. On the other hand, at 500 keV, the refractive index raises to $4.2 \times 10^{-8}$. Consequently, the time gain of a 10 keV photon passing through 30 cm of water compared to vacuum is approximately 55 femtoseconds, whereas the time gain through the same 30 cm of water is 22 attosecond at 500 keV (i.e., less than one attosecond per cm). Hence, the use of 511 keV gamma rays requires a level of accuracy in detecting that is extremely taxing.

Additionally, the gamma ray pairs do not move in directions that are exactly 180° opposite. Rather, there is approximately a 10 milli-Radian deviation of the gamma rays from exactly opposing paths. Hence, the system 60 described with respect to FIG. 5 may not readily result in images that are desirable for clinical or medical application. However, it may result in images that are suitable for industrial applications involving thick, or highly attenuating, materials.

Therefore, the above-described system 60 includes the use of a very small, low activity, positron-emission source 62. In this case, one of the gamma ray photons is used to generate a reference air transit-time image that provides a basis for comparison to the body transit-time image generated by its opposing gamma ray. This technique reduces uncertainty about the photon's launch time, but introduces an uncertainty due to the non-colinearity of the two gamma rays. Furthermore, the energy of the emitted photons should be in excess of 500 keV, which results in less efficient detection and reduced refraction.

Figure 6:
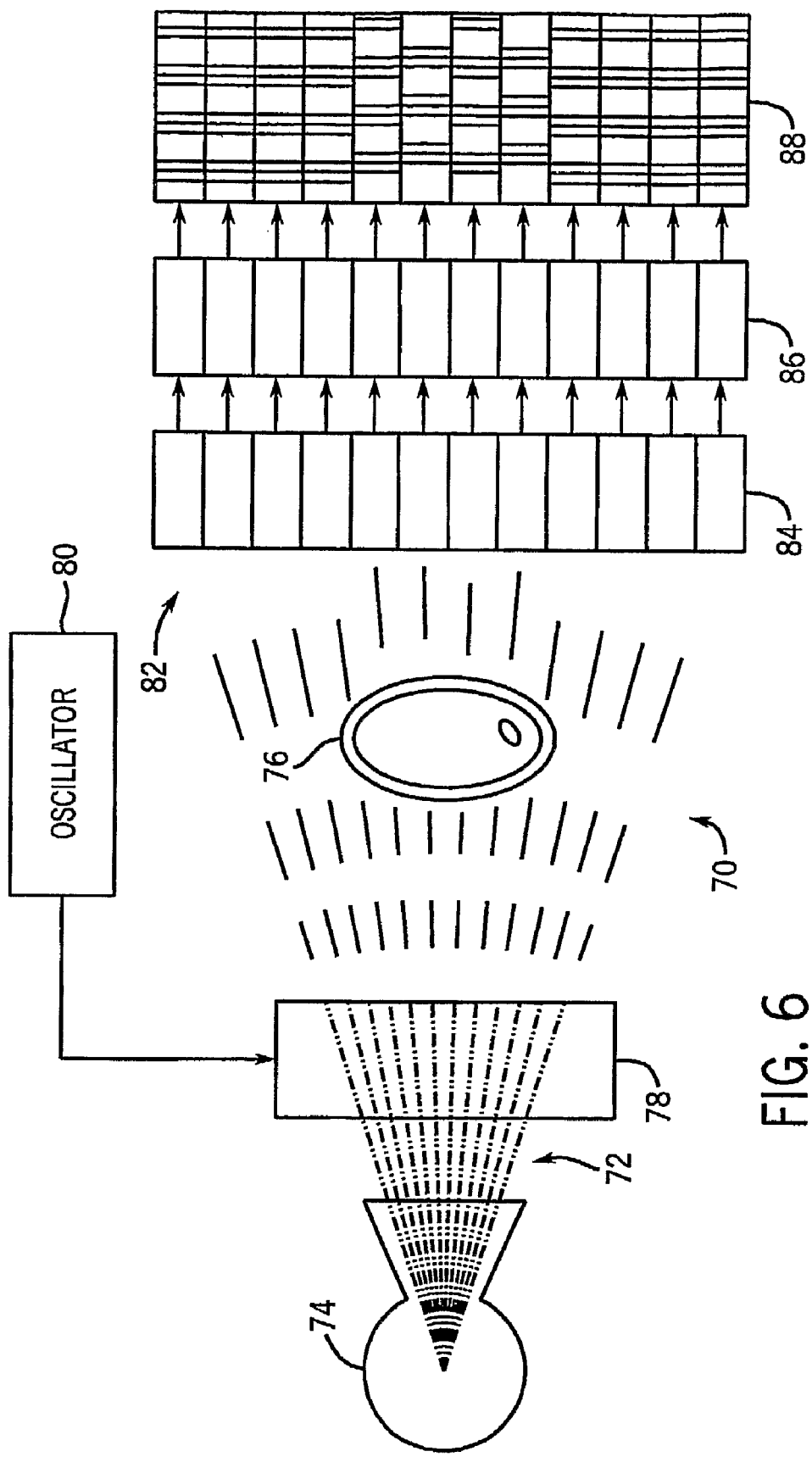
FIG. 6 is a schematic representation of yet another system for performing time-of-flight x-ray imaging.

Referring now to FIG. 6, another system 70 for performing TOFI employs an intensity-modulated x-ray beam 72 emitted by an x-ray source 74. The x-ray source 74 includes a field-emission tube that can generate x-ray pulses having a sub-nanosecond duration. Alternatively, the x-ray source 74 may be a continuous x-ray source, such as from a radionuclide, which is advantageously monochromatic.

The x-ray beam 72 is directed toward a subject 76. Arranged between the x-ray source 74 and the subject 76 is a modulator 78, such as a piezo-electric crystal, that can be controlled by an oscillator 90 to cycle its thickness at an accurately controlled amplitude and frequency. Alternatively, the modulator 78 may include a rapidly rotating wheel containing many holes along its periphery that likewise serves to modulate the x-ray beam 72.

The x-ray beam 72 passes from the modulator 78 toward the subject 76 and, ultimately, a detector system 82. In a manner akin to that used in light transmission "ballistic" imaging, the phase shift of the detected x-rays, relative to the modulation of the launched x-rays, can then be used as an estimate of the phase shift of the individual x-ray photons. Hence, the detector system 82 includes an x-ray to electron converter array 84 coupled to an A/D converter 86 that provides the digitized signal to a list mode memory module 88.

In operation, the cyclically modulated intensity of x-ray beam is directed toward the subject 76 and the phase delay of the modulated beam at each pixel of the detector system 82 is measured. In a manner similar to that described with respect to FIG. 2, the x-rays passing along the side of the subject 76 are used as the timing reference and the distribution of delays associated with a "no-body" image are used as the normalization mask to correct for any differences in the performance of each detector pixel. However, unlike the systems described above, it should be noted that this system 70 has an increased susceptibility to contamination by scattered x-rays and may require additional systems, such as collimators, grids, and the like to produce suitable images.

All three of the systems described above have two common technical aspects. In particular, a sufficient number of photons must be detected to ensure that each pixel in the imaging array has identified at least a minimum number of detections necessary to establish the transit time through the body with the desired temporal resolution. This minimum number of detections is largely determined by the time-distribution of the probability of each photon's launch, the detection of each photon, and the timing allocation of each photon.

Also, very fast x-ray detection arrays and electronic processing systems are necessary to implement each system because time delays on the order of femtoseconds or even sub-femtoseconds must be accurately measured to achieve spatial resolutions of approximately 1 mm. However, even though the clocks and detection mechanisms are limited in frequency and stability and the temporal distribution characteristics of the launched x-rays introduce additional variation in the detection of the photon arrival-time, the measurement of a number of x-ray photon arrival-times can be used to get a statistically sound estimate of the transit time. Moreover, temporal resolution greater than the frequency of the governing clock and the inherent variation in photon-detection time within the detector system, can be achieved.

In particular, an x-ray photon traverses the average human torso in approximately 1 nanosecond and traverses 1 mm in $3.3 \times 10^{-12}$ seconds (i.e., 3.3 picoseconds). Hence, the response time necessary to measure the time of flight of an x-ray photon is much greater than is currently achieved with traditional systems that are designed to measure the time of flight of various rays, for example, time-of-flight PET scanners. For example, if the velocity of x-ray through water differs from air by approximately $10^{-4}$, then the presence of one extra mm of tissue would delay the photons arrival by 330 attoseconds. Thus, imaging of just the presence or absence of tissue at 1 mm resolution would require time discriminations in the sub-femtosecond range.

Furthermore, differences between tissue types affect the velocity of x-ray, predominantly, via density variations. Since tissue variations range from 0.916 g cm$^{-3}$ for fat to 1.026 g cm$^{-3}$ for blood and 1.99 g cm$^{-3}$ for cortical bone, the difference in transit time for discriminating soft tissues at the 1 mm spatial resolution level requires detection of a 10% change in transit time (i.e., 30 attoseconds). Uncertainty in the velocity measurement would require a number of repeat measurements to provide a degree of certainty.

Figure 7:
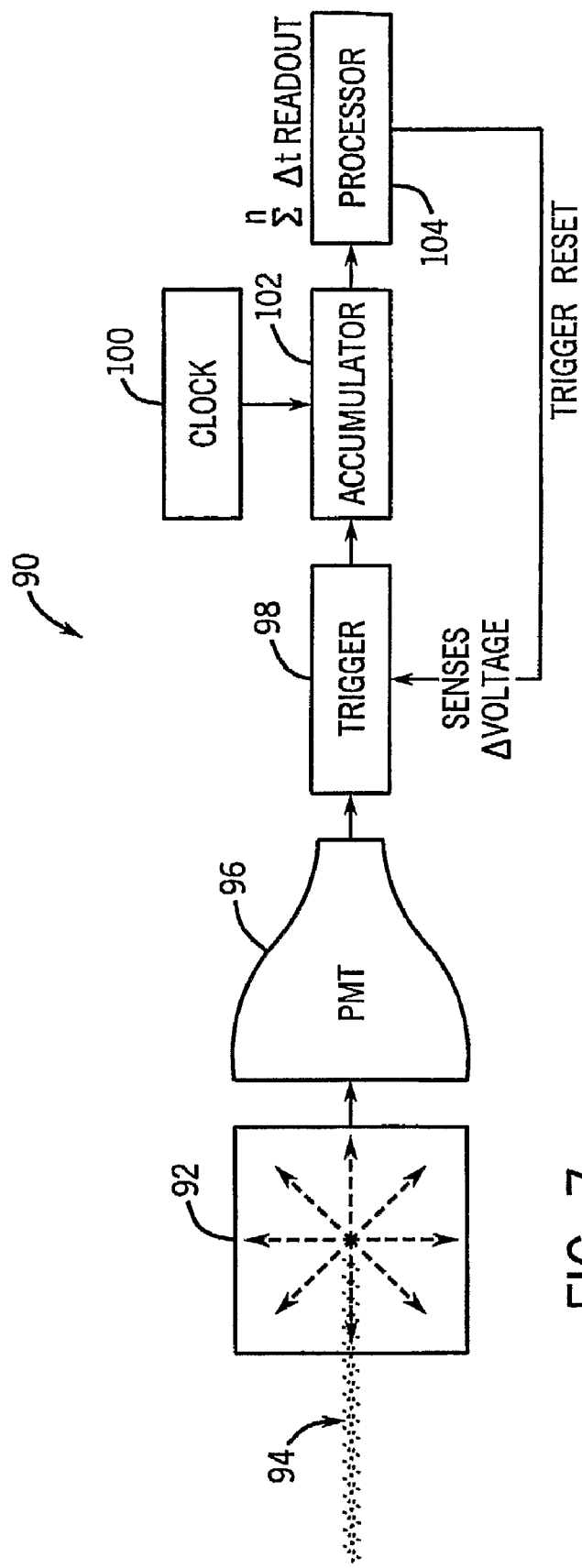
FIG. 7 is a schematic representation of a scintillator-based detector system for use with a time-of-flight x-ray imaging system.

Hence, referring to FIG. 7, a new detector system 90 is provided that is capable of discriminating between variations in the sub-femtosecond range and, in particular, into the range of multiple attoseconds. The detector system 90 includes a crystal of, for instance, Cerium-activated Lutetium Orthosilicate (LSO) 92 designed to receive photons 94 and deliver the detected photons to a photomultiplier 96. The photomultiplier 96 then converts the light to electrons that are delivered to a trigger 98, for example, a Schmitt trigger. The trigger 98 is designed to switch when the photomultiplier 96 indicates the presence of a detected photon. The trigger 98 should be very stable and have hysteresis so that a noise signal does not result in "chatter".

The sub-femtosecond time difference that must be detected and measured can be estimated with a clock 100 having multi-femtosecond time resolution by counting over many photons (of known time-dispersal). An accumulator 102 adds up the pulses from the clock 100 until the trigger 98 switches and "freezes" or stops the accumulation. The accumulator 102 holds the time of each photon detection event. A processor 104 receives the total calculated by the accumulator 102 and calculates the difference between the accumulated value and a stored reference value corresponding to the time delay resulting from passage of photons to the detector in the absence of an imaging subject.

At lower photon energies, the time delay increases, thereby, making the arrival time measurement more practical. However, it should be noted that this results in an increase of more than tenfold in the amount of x-ray exposure needed to overcome the increased attenuation of photon flux and maintain the sufficient number of photons that must be transmitted through the body.

The detector system 90 introduces some variables that should be taken into account. For example, the LSO crystal 92 adds a delay to the system as a photon passes through the crystal 92 and before it interacts and generates a light pulse. Additionally, further delay is incurred by the photomultiplier 96 as it converts the light to an electronic signal.

LSO scintillators are commonly used as a gamma ray detector in positron emission tomography (PET) because of its combination of decay speed and its quantum efficiency. Within time-of-flight PET, the LSO detectors are used to constrain the location of the positron annihilation, which requires a coincidence time resolution of 300 picoseconds (i.e., 160 picoseconds for each of the two crystals). Such resolution is achievable using LSO detector if details about the surface finish are known (e.g., polished or etched) and consequent intra-crystal reflections as well as crystal size are optimized.

Within the present invention, LSO crystal 92 is used to measure the refractive index characteristics of the tissue the photon traverses, as opposed to simply constrain the location of the positron annihilation. In this case, if the LSO detector has a 1.2 cm attenuation length, it should be designed to discriminate new photons at 27-40 picoseconds (assuming a light collecting efficiency of 50% and a quantum efficiency of 20%). However, if the crystal depth is decreased to one tenth, the time window within which the photon must have interacted with the crystal is also reduced tenfold (e.g., from 40 ps to 4 ps). By reducing the crystal depth, a considerable reduction in the percentage of photons detected is incurred. This signal is further delayed by the light-to-electron conversion within the photomultiplier 96, with a certain time-spread of uncertainty. However, this time-spread can be readily characterized.

In particular, the time spread of the inherent delay in the detection system affects the A/D converter signal. Consequently, many photons need to be detected to provide a reasonable estimate of the arrival time. This characteristic probability of detection-time pattern is then be used to get "super-resolution" time delay estimates, as illustrated in FIGS. 4a-4d. The chance of the photon reaching a certain depth within the LSO crystal is exponentially related to the distance the x-ray photon must pass through the crystal before it interacts to generate a light pulse.

If a very thin crystal is used, the impact of this time delay is minimized. However, as the crystal thickness is reduced, the fraction of the photons that pass through that thin crystal and are not detected is increased. In addition, for the positron-annihilation-based system described above with respect to FIG. 5, even if the photon is stopped in the thin crystal imaging detector, it might not be stopped by the associated reference detector. On the other hand, if a very thick LSO crystal is utilized, almost all photons are stopped. However, it would become increasingly difficult to determine where within the crystal a photon was stopped, which results in uncertainty in the time-delay measurement and increases errors with respect to the reference signal.

Figures 8A, 8B:
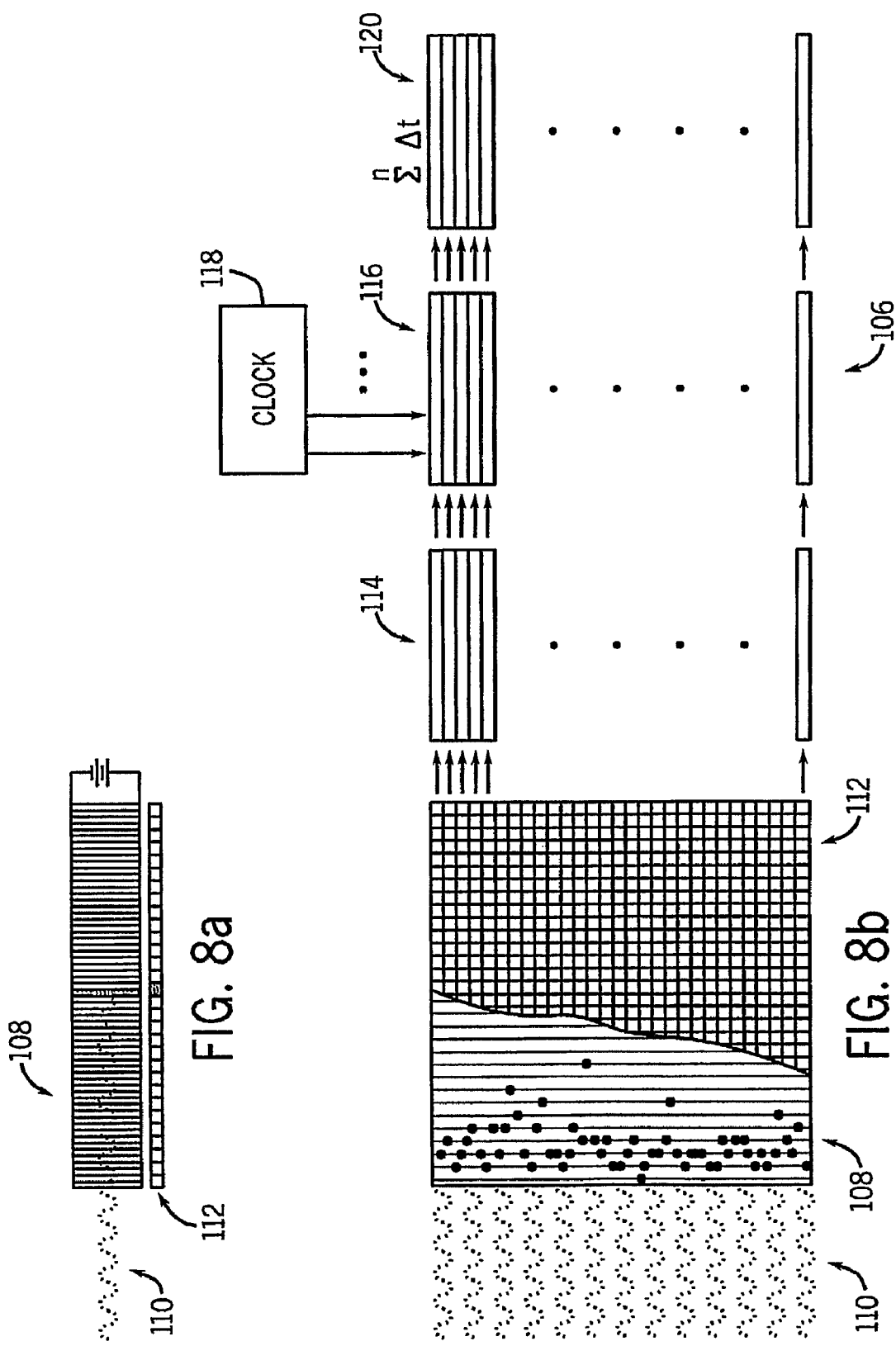
FIG. 8a is cross-sectional representation of a scintillator/photo multiplyer-based detector for use with time-of-flight x-ray imaging system.
FIG. 8b is a schematic representation of a microchannel plate intensifier (MCPI)-based, detector system incorporating the MCPI-based detector of FIG. 8a for use with a time-of-flight x-ray imaging system.

Alternatively, referring to FIGS. 8a and 8b, a direct, x-ray-photon-to-electron, current-conversion system 106 could be used instead of the LSO crystal of FIG. 7. The system 106 includes a micro-channel plate image intensifier (MCPI) 108, which, traditionally, is designed to be illuminated face-on with x-rays. However, with in the illustrated system 106, the MCPI 110 is arranged to receive x-rays 110 side-on. The MCPI is made up of 2-25 μm diameter hollow leaded glass capillaries that have a high voltage source 109 applied across lengthwise. In operation, when an x-ray interacts with a wall of the MCPI 108, the electron that is released is amplified by the voltage gradient applied by the high voltage source 109. Accordingly, the electron is accelerated and knocks additional electrons from the glass surface to generate an electron "shower". In particular, the MCPI 108 may generate approximately $10^4$ electrons within 200 picoseconds. For example, assuming the MCPI 108 has a 25 mm diameter and 90% attenuation, it would have a time range of about 80 picoseconds.

The MCPI 108 is arranged to receive the x-rays "side-on" so that the photons pass transversely to the glass capillaries of the MCPI 108. Thus, instead of using the depth of penetration as an index of x-ray photon energy (such as might be used when discriminating the primary radiation from scattered radiation), the depth of penetration of the photon can be related to into the delay from the time of transit through the face of the detector. If 3 μm capillaries are used, the potential temporal resolution (by virtue of position) is 10 femtoseconds. Thus, the probability of x-ray interactivity with a particular micro-channel falls off exponentially and scattered radiation arrives much too late to interfere with accurate detection. As will be described, this value is equivalent to the accumulated count generated by the Schmitt-triggered accumulation process.

An array of charged coupled devices (CCD) 112 is coupled to the MCPI 108 to convert the light received by the MCPI 108 into electrical current. In particular, the CCD 112 is arranged as an array abutting the face of the MCPI 108. Hence, the CCD array 112 is activated by the cascade of electrons generated by the MCPI 108. By noting the position within the CCD array 112 where the charge was generated, the precise depth of penetration of the photon into the MCPI 108 can be determined. As such, the time interval between entry of a photon into the MCPI 108 and the interaction can be determined.

The CCD array 112 is connected to a corresponding array of triggers 114 (one per CCD row). In a manner similar to the photomultiplier 96 of FIG. 7, the CCD array 112 activates the trigger 114, which, in turn, stops an accumulator 116 from adding the pulses from a high frequency clock 118. That is, the accumulator 116 adds up the pulses from the clock 118 until the trigger 114 switches and "freezes" or stops the accumulation. As such, the accumulator 116 holds the time of each photon detection event. A processor 120 receives the total calculated by the accumulator 116 and calculates the difference between the accumulated value and a stored reference value corresponding to the time delay resulting from passage of photons to the detector in the absence of an imaging subject. Thus, in both of the above described systems, for each photomultiplier 96 or row of CCD detector pixels 112 there is an accumulator 102/116 that adds the clock pulses until a detected event activates a Schmitt trigger-like device and "freezes" the accumulation.

Improved temporal resolution above the discrete steps of the above-described scintillator-based and the MCPI-based systems can be achieved by advantageously utilizing the x-ray pulse spread, which is operational in both the scintillator and MCPI approaches. Temporal resolution can be further improved in the above-described scintillator-based system and the MCPI-based system by virtue of the "dithering" of the time signal caused by the different depths of penetration in the LSO crystal or the spread in "amplification" times of each capillary of the MCPI, respectively. The "dithering" effect results in a time discrimination $\Delta t<$(clock cycle duration)/$(\pi 2^{\#A/D\ units})$, where the temporal cycle length is 10 femtoseconds in both the scintillator and MCPI cases.

Using these systems, bias due to detector-specific electronic delays and the like can also be quantitated by imaging without the body in place. For example, if the clock has a cycle time of $\delta T$ seconds (e.g., 1 femtosecond), and there is a spread in the detected arrival times of the photons (due to detector thickness or due to the temporal spread of the x-ray pulse), assuming a Gaussian distribution with 1 SD=$k\delta T$, where k>1, then with 128 observations it is possible to measure a time interval of 0.1 $\delta T$. Approximately 1000 observations would bring this down to 0.01 $\delta T$ (i.e., 10 attoseconds), which is of the discrimination time order needed for detection of an extra millimeter of tissue path length.

Therefore, a system and method is provided for utilizing time-of-flight information of x-rays passing through a subject to generate diagnostic images of the subject. The above-described invention allows direct measurement of the refractive index (i.e., ratio of x-ray velocity through matter as compared to velocity through a vacuum) of x-rays through a body acquire data that can be reconstructed into an image of the body.

The present invention is capable of reducing x-ray exposure by orders of magnitude, because the contrast conveyed by the refractive index of x-rays through soft tissues is considerably greater than that obtained with traditional x-ray imaging. Consequently, the present invention enables imaging at doses suitable for the imaging of even asymptomatic patients. Hence, patients that are at risk of developing diseases, for example, by virtue of family history and/or exposure to a disease-causing environment, but would traditionally not be imaged since no symptoms have manifested that would justify exposure to the dose of a traditional imaging system, will be able to be imaged as a precautionary measure. Similarly, infants and children, who are particularly vulnerable to the deleterious effects of radiation, will be able to be imaged without concern. Hence, these populations can now be evaluated without the negative consequences of cumulative radiation effects due to repeated whole body imaging, for example, CT scans.

The present invention has been described in terms of the preferred embodiment, and it should be appreciated that many equivalents, alternatives, variations, and modifications, aside from those expressly stated, are possible and within the scope of the invention. Therefore, the invention should not be limited to a particular described embodiment.

The invention claimed is:

1. A system for producing diagnostic images comprising:
    a clock generating a clock signal;
    a radiation source directing photons through a subject to be imaged;
    a detector system detecting the photons;
    a memory module recording a time of detection of the photons by the detector system with respect to the clock signal; and
    a processor calculating a time of flight (TOF) of the photons to the detector system and comparing the TOF to a reference TOF to determine a delay in the TOF attributable to the photons passing trough the subject.

2. The system of claim 1 further comprising means for reconstructing an image of the subject based on the delay in the TOF attributable to the photons passing trough the subject.

3. The system of claim 2 wherein pixel intensity in the reconstructed image is a function of the delay in the TOF attributable to the photons passing trough the subject.

4. The system of claim 1 wherein the radiation source includes a pulsed laser source and electron beam source arranged to collide a laser beam and electron beam together to generate an x-ray pulse directed toward the subject.

5. The system of claim 1 wherein the radiation source includes at least one of a field-emission tube generating x-ray pulses having sub-nanosecond durations and a continuous x-ray source modulated by a modulator arranged between the radiation source and the detector system to modulate the x-rays passing through the subject.

6. The system of claim 1 wherein the processor sums a number of contiguous time slots to generate a frequency histogram and therefrom estimates a time of arrival of the photons at the detector system.

7. The system of claim 1 further comprising an accumulator monitoring the clock signal to generate a metric indicative of the TOF.

8. The system of claim 7 further comprising a trigger coupled to the detector to freeze the accumulator when a photon is detected to generate the metric and provide the metric to the processor.

9. The system of claim 8 wherein the trigger includes a Schmitt trigger.

10. The system of claim 1 wherein the detector includes an LSO crystal coupled to a photomultiplier.

11. The system of claim 1 wherein the detector includes a micro-channel plate image intensifier (MCPI) and a charge coupled device array.

12. The system of claim 11 wherein the MCPI detector includes a plurality of glass capillaries arranged to detect photons traveling transversely to the glass capillaries.

13. A method for producing an image of a subject, the method comprising the steps of:
    a) directing photons through a subject from one side of the subject;
    b) detecting the location of the photons passing through the subject to another side of the subject opposite the one side of the subject;
    c) measuring a time of flight (TOF) of the detected photons; and
    d) comparing the TOF of the detected photons to a reference TOF to determine a delay incurred by the photons by passing through the subject; and e) reconstructing an image of the subject using the location and the delay incurred by the photons passing through the subject determined in steps b) and d).

14. The method of claim 13 wherein step a) includes generating the photons using a positron annihilation source.

15. The method of claim 13 wherein step a) includes generating the photons using at least one of:
- a pulsed laser source and electron beam source arranged to collide a laser beam and electron beam together to generate an x-ray pulse directed toward the subject;
- a field-emission tube generating x-ray pulses having sub-nanosecond durations directed toward the subject; and
- a continuous x-ray source modulated by a modulator arranged between the radiation source and the detector system to modulate the x-rays passing through the subject.

16. The method of claim 13 wherein step e) includes selecting a pixel intensity for each pixel in the reconstructed image based on the delay incurred by the photons passing through the subject.

17. A system for producing diagnostic images comprising:
- a radiation source including a positron annihilation source disposed to one side a subject to direct photons through a subject to be imaged;
- a reference detector array arranged on the one side of the subject to receive first gamma rays produced by annihilation events;
- an image detector array arranged on a side of the subject opposite the one side of the subject to receive second gamma rays produced the annihilation events after the second gamma rays pass through the subject;
- a processor calculating a time of flight (TOF) difference between receiving the first gamma rays at the reference detector and the second gamma rays at the image detector; and
- means for reconstructing an image of the subject based on the TOF difference.

18. The system of claim 17 wherein pixel intensity in the reconstructed image is a function of the TOF difference.

19. The system of claim 17 wherein the reference detector and the image detector include an LSO crystal coupled to a photomultiplier.

20. The system of claim 17 wherein the reference detector and the image detector includes a micro-channel plate image intensifier (MCPI) and a charge coupled device array.

* * * * *